United States Patent [19]

LeVeen et al.

[11] Patent Number: 4,662,404
[45] Date of Patent: May 5, 1987

[54] FLEXIBLE TUBING

[76] Inventors: Harry H. LeVeen, 312 Confederate Cir., Charleston, S.C. 29407; Eric G. LeVeen, 3-3 Woodlike Rd., Albany, N.Y. 12203

[21] Appl. No.: 264,061

[22] Filed: May 15, 1981

[51] Int. Cl.⁴ ............................................. F16L 11/12
[52] U.S. Cl. .................................. 138/120; 138/118; 138/155; 138/177; 138/178; 128/348.1; 428/36
[58] Field of Search ............... 138/118, 137, 140, 177, 138/178, 120, 155; 128/2 M, 348, 349 R; 428/36

[56] References Cited

U.S. PATENT DOCUMENTS 3,605,750  9/1971  Sheridan et al. ............... 138/155 X
3,752,617  8/1973  Burlis et al. ..................... 138/137 X Primary Examiner—James E. Bryant, III
Attorney, Agent, or Firm—John S. Hale

[57] ABSTRACT

Flexible tubing suitable for medical use is disclosed having a set of relatively stiff sections intercalated with a set of relatively flexible sections, each flexible section having a length no greater than twice the diameter of the tubing.

1 Claim, 5 Drawing Figures

FLEXIBLE TUBING

This invention relates to flexible tubing which is particularly suitable for medical use, such as in catheters and the like, and provides a tubing construction and a method of extruding such tubing.

In surgical and other hospital practices of medicine, the use of flexible tubing is necessary and commonplace. Tubes are used for catheters, for nasogastric suction, for administration of intravenous fluids and blood, to mention but a few cases. Occasionally, tubing is implanted in the body permanently as in the treatment of hydrocephalus by drainage of spinal fluid into the venous system or peritoneal cavity or in the treatment of ascites by drainage of ascitic fluid with a peritoneovenous shunt. At other times tubing is temporarily inserted, as for taking venous pressure, or for infusing concentrated gluclose solution into the vena cava.

Generally, there are a number of problems which are encountered in the use of flexible tubing for purposes which will be discussed in this application. One of these is the problem caused by unnoticed, inadvertent kinking. Another problem arises from the need, particularly where the tubing is inserted or implanted within the body, to ascertain the location of the center of the tubing, for example, by radiography. Another problem is inadvertent knot tying of catheters due to unlimited bending of the tubing. Still another problem is to rigidify the walls without the incorporation of reinforcing wire which increases the cost of the tubing.

Generally, tubing which is sufficiently flexible for medical use, as described above, must be constructed of material which is relatively flexible and must be constructed with relatively thin walls, not only to permit the necessary flexibility but also to accommodate flow through the tubing. Such tubing is subject, upon bending, to kinking and consequently collapse and blockage of flow. When the kinking inadvertently occurs and is unnoticed, the tubing ceases to function with consequences that can be fatal.

It has heretobefore been proposed in utilizing tubing, either introduced into or implanted within the body, that the tubing be made radiopaque. This usually results in tubing which is not optically translucent, and therefore presents problems in determining the presence and position of foreign matter and the like when the tubing is cleaned and sterilized. Also, such tubing cannot be opacified by the injection of radiopaque contrast agents which is often required to check the position of the tube in the body and also to determine the presence of obstructions distal to the tubing. One solution to the latter problem is the coextrusion of a radiopaque stripe in the wall of otherwise optically translucent and radiolucent tubing (U.S. Pat. No. 2,857,915) but such stripes do not give an indication of the size of the lumen, and hence of its center, and also are a poor indication that a section of tubing has kinked. A stripe gives no indication as to the length of the tubing in any particular part of the body.

In copending LeVeen application Ser. No. 720,994, filed Sept. 7, 1976, the problems of kinking of tubing inserted in the body and of observing such tubing by radiography are basically solved by coextrusion of tubing having a generally homogeneous tubular wall section composed of a relatively flexible material, in which there is embedded a helical strand of relatively stiff, resilient material, extending lengthwise of the wall portion along a helical path about the wall portion. Radiopaque materials are incorporated either in the wall portion or in the strand portion, and the other portion is formed of optically and radio-translucent material. Preferably, the radiopaque materials are incorporated in the strand portion.

While such tubing having a helical, stiff and radiopaque strand has many advantages over existing tubing, there is no way to determine the exact length of tubing which has been introduced into the body. This is so partly because the radiograph amplifies an image of an object which is a distance from the film. The amplification differs as the distance of the X-rayed object from the X-rayed film varies. Also, the tubing may extend on an angle or even be perpendicular to the X-rayed film, thus preventing any measurement.

Another difficulty with the use of flexible plastic having a helical, radiopaque stiffener is that a rotating die is required for coextrusion of the two plastic materials. Such a manufacturing technique is complicated and has serious mechanical limitations.

Knotting is another common problem with tubing which is introduced into a body cavity. For instance, when a nasogastric tube is introduced into the stomach, the tube can coil in the stomach and the tip of the tubing can enter the coil and thus form a single throw knot. When attempts are made to remove the tubing, the knot is drawn tight and withdrawal of the tubing through the esophagus is prevented. Thus, when a knot is tied in the stomach it may be impossible to remove the tubing without surgery. Similarly, knots have been tied in tubing which is introduced into the heart, the spinal canal, pleural cavity, abdomen, and urinary bladder. It is possible for a knot to form when the space into which the tubing enters is large enough to allow a single coil to form within its cavity.

While tubing for such medical uses is desirably flexible, stiffness is an essential property for some tubing such as angiographic catheters where it is necessary that the tube be relatively rigid in order to advance it in the vessel and prevent its kinking and coiling. This is usually accomplished by placing a stiff guidewire in the center of the otherwise flexible tube. Stylettes and rigid introducers are also used in introducing endotracheal tubes. With endotracheal tubes, the tube must not be collapsible but also should be kink proof. It would be ideal if such tubes could be introduced without the necessity for stylettes. Catheterization of the bladder in males is often difficult because the tubing is so soft that it cannot be passed through the prostate gland which offers resistance. Catheters are usually so soft that they bend outside the body rather than in the narrow urethra. Hence flexible tubing which possesses a degree of stiffness would be easier to introduce.

Another property which is useful in medicine, is that the tubing be collapse proof from external pressures. When such collapse proof flexible tubing is required, it is customary to utilize tubing which is relatively rigid or has a reinforcement in the wall. Intravenous catheters and cannulas frequently undergo kinking, and intravenous infusion is inadvertently interrupted either temporarily or totally. This not infrequently happens when the patient bends his elbow or moves his body in such a way so to kink the tubing or to compress the tubing with adjacent tissue. Thus, tubing for intravenous use should be not only non-kinkable, but non-compressible once it is in the vein. Semi-rigid tubing which is presently used for this purpose can be inadvertently kinked with the result that stoppage of infusion occurs.

Special catheters are use in the heart during open heart surgery. These cannulas frequently have circular wires or circular extrusions incorporated into them to prevent their kinking or collapsing. The result is less than satisfactory since flexibility is sacrificed in order to obtain tubing which is rigid enough to introduce.

It is an important object of this invention to provide tubing for medical purposes which can have the advantages of flexibility while having a sufficient degree of stiffness and rigidity to minimize kinking to prevent collapse and to eliminate knotting.

In accordance with these objects, the tubing of the invention also permits incorporation of radiopacifiers in a manner which will show the full width of the lumen but which will still permit visual inspection of the interior of the tubing.

In accordance with the present invention, two or more conventional plastic extruders are arranged to extrude into a common die in an alternating fashion. The extruders extrude plastic materials of different durometer hardness. One of the plastic materials can be radiopaque and the other optically translucent and radio-lucent. If three or more extruders are used, different degrees of radiopacity and stiffness are possible. In the simple case of the two extruders, the extruders are so arranged that extrudate is delivered to the die alternating from one extruder to the other at regular intervals so that the resultant tubular extrusion is banded at uniform intervals. In the preferred case, this gives the tubing a final appearance of having a series of radiopaque bands or rings at uniform intervals so as to create a measuring system with each small band of stiffened plastic occurring at a fixed distance from the previous band. Thus, by means of X-ray technique, the stiffening bands within the body can be counted providing a measure of the length of tubing within the body. If desired, every fifth or tenth band can be widened to create a scale simplifying the count.

In actual practice, it is not satisfactory to run an extruder intermittently. Therefore, each extruder is allowed to function continuously but the output of the extruder is alternately directed to the die and to a dump. The dump should be preferably through a restriction creating a back pressure equal to that in the die. By the word "dump", it will be appreciated, recycling or other use of the extruder output is contemplated. Recycling generally can take two forms. In some case, it is permissible to recycle directly back through the extruder barrel. In others, it may be necessary to permit the dumped material to harden, regrind it and then reintroduce it into the hopper of the extruder. Two or more extruders can also be set up so that they feed two or more dies, each forming a length of flexible or rigid tubing, with the extruder outputs being alternated between the tubing dies such that when one extruder is extruding through one die, the second extruder is extruding through another die, and vice versa.

Switching of the extruders can be accomplished simply utilizing a solenoid operated valve, such that the switching is rapid. In this manner, pressure developing in the extrusion die can be kept relatively constant and it is unnecessary to interrupt the function of the machine to control its output. If the switching is prolonged a pressure accumulator must be placed in the circuit. This is usually unnecessary but may be desirable.

Utilizing this technique, the resulting product is a tubing with a series of interrupted circumferential reinforcements to prevent its collapse or kinking and which in the preferred case being radiopaque are visible under X-ray technology such that the presence of the tube can be located, the occurrence of kinking can be observed and the length of tubing within the body can be measured.

The flexible tubing of the invention is thus composed of a series of contiguous, tubular wall sections of melt-extrudable materials including a first set of wall sections separated from each other and formed of a relatively flexible material and at least a second set of wall sections separated from each other and formed of a relatively stiff, resilient material. Each of the wall sections of the first set is contiguous with a wall section of the second set, and where only two sets of wall sections are involved, obviously the wall sections of the two sets alternate.

Generally, the length of the sections of the first set, that is, the flexible wall sections, should be no longer than twice the diameter of the tubing. This consideration is necessary in order to minimize kinking.

If one is to make a soft pliable tubing section kink resistant, it is essential that the stiff sections be repetitively spaced at intervals no longer than two times the diameter of the tubing because two diameters is the length of tubing which is required for one side of the tubing to reach the opposing side. If the stiff section is repeated within this distance of two diameters, it is not possible for inside curvature of the tubing to reach the greater curvature side. The frequency of the stiff sections, as compared to the flexible sections, depends upon whether the flexible tubing is elastomeric or merely flexible and whether or not the tubing is thin walled or thick walled. Very thin walled tubing has more of a tendency to kink and collapse than thick walled tubing. In some applications, it is desirable to increase the number of rigid sections so that as many as three or four stiff sections of short linear length are present in the space of two diameters of the tubing. Such construction effectively renders the tubing kink proof and prevents narrowing of the tube on bending.

The foregoing discussion surmises that the tube is elastomeric or flexible and that repetitive sections of stiff plastic are to be repeated at some desired frequency. However, the tubing of the invention can also be looked upon as a rigid tubing with intercalated flexible or elastomeric sections. When flexibility is desired the wall sections of the second set, that is, the stiff wall sections should be relatively short compared to their contiguous flexible wall sections. However, where knotting is to be prevented and where stiffness is required, for example, to facilitate insertion of a catheter, the wall sections of the stiff set can be relatively longer, and in extreme cases substantially longer, than the wall sections of the flexible set, the ratio of the length of the flexible wall sections to the length of the stiff wall sections being determined by the degree of flexibility required.

A configuration in which such ratio is low is especially useful in that it prevents the tubing from undergoing sharp flexural bending. This limits the acuteness of angulation which is possible. Making the tubing stiff with small intercalated sections of flexible material, limits the flexural bending which the tube can make and renders it impossible for the tube to coil in a cavity into which it is introduced. Thus, it will be seen that stiff tubing with small intercalated sections of flexible or elastomeric tubing can have unique properties which are useful in medicine. The tubing can thus be rendered relatively stiff. Obviously, tubing with short flexible sections between stiff sections acts like an articulated rigid tube, a hinged tube, and can be sufficiently stiff so that it can be passed through a vessel or introduced into a body cavity without the necessity of using a guidewire, stylettes stents or rigid introducers.

A particularly satisfactory tubing for intravenous catheters or cannulas is one which has stiff sections alternating with short flexible intervening sections so that the tubing is rigid enough to introduce and yet flexible and whose lumen can not be comprised by acute bending or kinking. Thus, it can be seen that the use of repetitive segments of hard and soft materials from two or more extruders can produce physical properties of the tubing which fulfill many vital needs in medicine. In the case of some catheters, such as vascular catheters, the catheter should have a flexible tip but the body of the catheter should be relatively rigid and formed of repetitive hard segments. In this case, it is possible to extrude a long flexible tip and then to repetitively extrude hard and soft segments of plastic. This fulfills the need for a flexible tip and at the same time fulfills the need for a stiff, non-kinking shank. Such programed extruding is possible to provide some specialized needs and is an object of this invention.

For a more complete understanding of the practical application of this invention, reference is made to the accompanying drawing in which.

Figure 1:
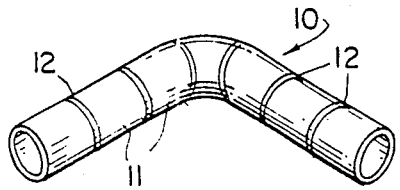
FIG. 1 is a view illustrating a length of flexible tubing according to the present invention.

In the drawings, the reference numeral 10 designates a section of flexible tubing in accordance with the present invention. Tubing 10 basically includes a set of tubular wall sections 11 formed by extrusion, preferably of a melt-extrudable material, such as silicone rubber, which after cooling sets to a relatively flexible homogeneous structure. Each section 11 has a length not greater than twice the diameter of tubing 10. Sections 11 alternate with another set of tubular wall sections 12, which are relatively short in relation to wall portions 11, and which are formed by extrusion of a different silicone rubber which when set is highly stiff and resilient and in which is incorporated, a radiopaque pigment, such as calcium carbonate, barium sulfate, bismuth oxychloride or the like. As can be seen with reference to FIG. 1, when tubing is bent, flexure does not produce kinking because of the stiffening effect of tubular sections 12. It should be pointed out again that the stiff and flexible sections can be revised to produce a more rigid tube with limited flexibility.

Figure 2:
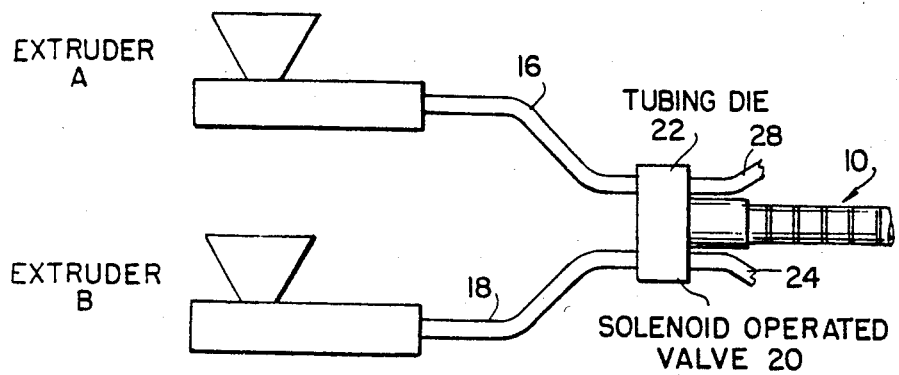
FIG. 2 is a schematic diagram of an apparatus setup suitable for forming flexible tubing in accordance with this invention.

Referring more particularly to FIG. 2, an apparatus arrangement for forming flexible tubing 10 is illustrated. Two conventional extruders designated "A" and "B" are connected by means of conduits 16 and 18 respectively to a solenoid operated valve 20 such that the outputs of extruder A and extruder B are directed into the valve 20, as more specifically described with reference to FIG. 3 and 4. Valve 20 is operated intermittently at regular intervals. In the unenergized position of value 20 shown in FIG. 3, the output of extruder A is directed through valve 20 to tubing die 22, and the output through extruder B is directed through valve 20 to recycle line 24. In the energized position of valve 20, i.e., when solenoid 26 is actuated, valve 20 connects the output of extruder A to recycle line 28 and connects the output of extruder B through die 22, as shown in FIG. 4.

Figure 3:
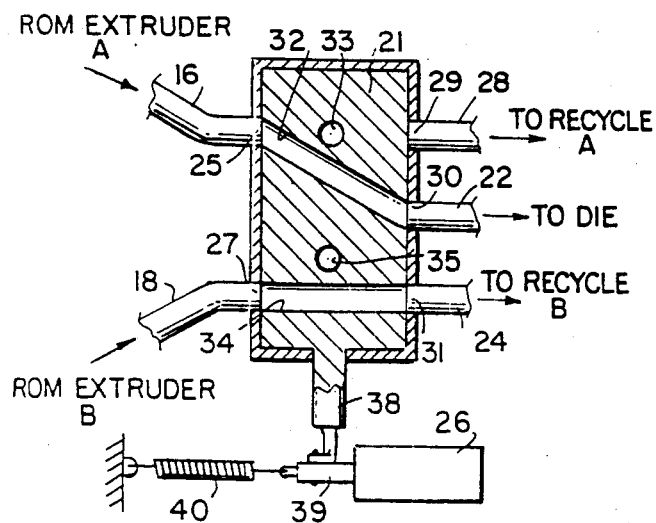
FIG. 3 is a schematic view partly in cross section of a solenoid operated valve illustrating one mode of operation of the apparatus shown in FIG. 2.
Figure 4:
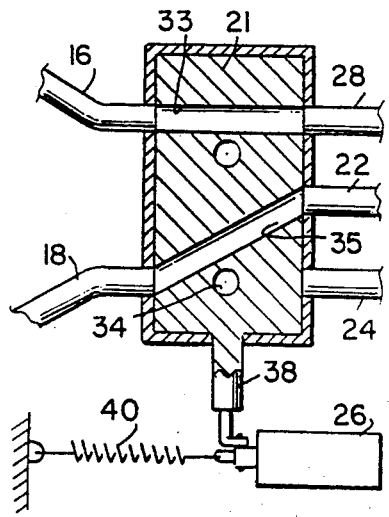
FIG. 4 is a view similar to FIG. 3 illustrating the alternate mode of operation of the apparatus shown in FIG. 2.

In order to accomplish this, it will be noted referring more particularly to FIGS. 3 and 4, that valve 20 consists of a cylindrical valve body 21 mounted in a suitable casing 23 to permit it to rotate. Casing 23 is provided with a pair of input ports 25 and 27 to which output connections 16 and 18 of extruders A and B are respectively connected. Casing 23 is further provided with three output ports, 29, 30, and 31. Port 30 is connected to die 22, while ports 29 and 31 are respectively connected to recycle to extruders A and B.

In the illustrated case, valve body 21 is rotatable in valve casing 23 and contains passageways which are designed to connect the various ports depending on the relative rotational position of valve body 21 in valve casing 23. One passageway, designated by the reference numeral 32, in the unactuated mode of valve 20, interconnects ports 25 and 30 as shown in FIG. 3. Passageway 32 in the actuated mode shown in FIG. 4 makes no connection. A second passageway, designated 33, makes no connection in the unactuated mode of valve 20 but interconnects ports 25 and 29 in the actuated mode shown in FIG. 4. A third passageway, designated 34, connects port 27 with port 31 in the unactuated mode of valve 20 shown in FIG. 3 but makes no connection in the actuated mode of valve 20 shown in FIG. 4. The fourth passageway, designated 35, makes no connection in the unactuated mode of valve 20, but in the actuated mode shown in FIG. 4 interconnects ports 27 and 30. Valve body 21 is designated to rotate about a vertical axis through 90° to permit switching between the actuated mode and the unactuated mode of valve 20. This rotation is accomplished by means of solenoid 26 which is connected to a crank 37 mounted on an axial shaft 38 on valve body 21 such that armature 39 of solenoid 26 is pivotally connected to the end of crank 37. Coil spring 40 is connected between fixed structure and armature 39 and designed to pull armature 39 extended out of solenoid 26 to cause crank 37 to rotate shaft 38 and valve body 21 to the unactuated position shown in FIG. 3. When solenoid 26 is energized, armature 39 is retracted into solenoid 26 against the bias of spring 40 rotating valve body 21 from the position in FIG. 3 to that shown in FIG. 4, i.e., approximately 90°.

It will be thus evident that the actuation of solenoid operated valve 20 by energizing solenoid 26 reverses the normal mode of connection through valve 20 such that although in the unactuated mode, the output of extruder A is delivered through tubing die 22, in the actuated mode the output of extruder B is forced through tubing die 22 to form a band 12. Desirably, extruder B has its output connected through tubing die 22 only for an interval carefully regulated in time such that the spacing of bands 12 is uniform.

As indicated above, while the output through ports 29 and 31 can be used to recycle the extruded outputs of extruders A and B, respectively, optionally, these outputs can be connected to a separate extruding die to form a separate extruded flexible tubing exactly like tubing 10. In this case, however, the length is of bands 11 and 12 are reverse, and the resultant tubing is relatively stiff, although retaining some flexibility.

While combinations of melt-extrudable, compatible materials such as flexible and stiff, resilient silicone rubbers can be utilized to form wall sections 11 and 12, respectively, other materials and combinations can be employed. Polysulfone is particularly useful in combination with flexible silicone rubber wall sections 11 since polysulfone is exceedingly stiff and has an extremely high heat deflection temperature which is important in permitting heat sterilization. Other "engineering-type" plastics can be substituted for wall sections 12, using ethylene vinyl acetate copolymer to form wall sections 11 or vice-versa. Polybutylene, polypropylene and ultra high molecular weight polyethylene have sufficient rigidity to prevent kinking of the soft, more flexible ethylene vinyl acetate copolymer. In addition, many different grades of ethylene vinyl acetate copolymer are available some of which are extremely soft and flexible and can be combined with grades that are quite stiff and hard. Still other examples of combinations of melt-extrudable compatible materials include rigid vinyl stiff wall sections with a highly plasticized flexible vinyl thermoplastic flexible wall sections. Thermoplastic urethane plastics are specially suitable for this application because urethanes adhere well to other plastics and have a wide range of flexural modulus. In addition, glass fibers and other materials can be incorporated into plastics to stiffen them for the purpose of forming stiff wall sections. This technique is especially useful with flexible urethane plastic.

Generally, in accordance with this invention, the stiff and less resilient, i.e., rigid, engineering plastic-type material is utilized for form bands 12 which act as the backbone of the structure and maintain the radius of the relatively flexible plastic of wall sections 11 during flexion of tube 10; as illustrated with reference to FIG. 1. At the same time, the flexible plastic wall sections 11 can be kept clear, or at least optically translucent, to permit inspection to insure against the accidental inclusion of foreign material and to permit the observation of liquid flow. The radiopaque materials are added to the backbone, that is wall sections 12. In some circumstances, it can be more desirable to make wall sections 11 radiopaque and retain the rigid material 12 optically translucent, as for example to increase the radiopacity of the tubing for some applications, that is, to make the longer wall portions radiopaque and the shorter optically translucent. When the relative lengths of wall sections 11 and 12 are reversed in producing stiffer tubing, generally it is preferable to incorporate the radiopacifier in the shorter flexible sections.

Figure 5:
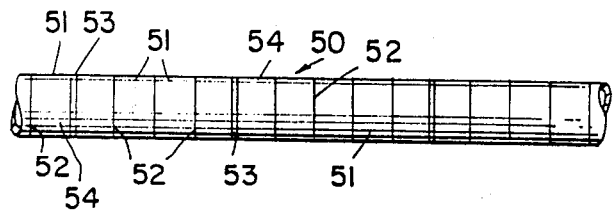
FIG. 5 is an elevational view of another length of flexible tubing in accordance with this invention.

As suggested above, it is desirable for certain applications to simplify counting of bands in measuring the length of tubing which has been inserted into the body by making every fifth or tenth band perceptibly wider than the others. This is illustrated in the drawings with reference to FIG. 5 where a length of flexible tubing 50 is illustrated composed of relatively long flexible tubular sections 51 which are separated by short stiff radiopaque bands 52. After four bands 52 have been formed followed by 4 longer lengths 51 in place of the next band 52, a wider band 53 is formed. This is done by actuating the solenoid operated valve 20 for a shortly longer period of time than used in forming bands 51. By keeping the initiation of energization of solenoid 26 at 52 and 53 along tubing 50 remains uniform. Consequently, the following extrusion of material from extruder A into die 22 will be for a slightly shorter period of time resulting in an intermediate flexible section 54 after each band 53 which is slightly shorter than sections 52. It will be evident that the perceptible difference between bands 52 and 53 greatly simplifies counting their total number.

While this invention has been described above in the specific context of manufacture of tubing for medical purposes, it will be apparent that it is not so limited. Tubing which is reinforced can be used for a variety of purposes such as garden hoses. Also, tubing which has alternating materials or a number of different materials repetitively positioned along its length can be desirable, for example, for decorative purposes, where the variation is in color of extruded material. Furthermore, the apparatus and method of this invention can be utilized for manufacturing products other than tubing, for example, rods marked at regular intervals for measurement purposes or to limit their flexibility. For instance, a series of rigid rods can be intercalated with elastomeric material in the manufacture of a fishing rod or other object where increased bending can be accomplished only with force and rigid plastics are liable to breakage.

We claim:

1. Flexible tubing comprising contiguous, tubular wall portions of melt-extrudable materials including one set of a plurality of wall sections and a second set of a plurality of wall sections in which each wall section of said one set is contiguous with a wall section of said second set, said wall sections of said one set being constructed of relatively stiff resilient material and being uniformly distributed along said tubing, and said wall sections of said second set being constructed of flexible material, each said wall section of said second set having a length no greater than twice the diameter of said tubing, and wherein certain of said wall sections of said one set differ perceptibly from the remainder of said wall sections and are located along said tubing separated from each other by a predetermined number of said remainder.

* * * * *